United States Patent
Auricchio et al.

(10) Patent No.: US 7,740,836 B2
(45) Date of Patent: Jun. 22, 2010

(54) METHODS AND COMPOSITIONS FOR RECOVERING OR IMPROVING VISUAL FUNCTION

(75) Inventors: Alberto Auricchio, Naples (IT); Enrico Maria Surace, Naples (IT); Andrea Ballabio, Naples (IT)

(73) Assignee: Fondazione Telethon, Rome (IT)

( * ) Notice: Subject to any disclaimer, the term of this patent is extended or adjusted under 35 U.S.C. 154(b) by 0 days.

(21) Appl. No.: 11/416,453

(22) Filed: May 3, 2006

(65) Prior Publication Data

US 2007/0258950 A1    Nov. 8, 2007

(51) Int. Cl.
*A61K 48/00* (2006.01)
*A01N 63/00* (2006.01)
*C12N 15/00* (2006.01)
*C12N 5/00* (2006.01)

(52) U.S. Cl. .................. 424/93.2; 424/93.1; 424/93.6; 435/320.1; 435/325

(58) Field of Classification Search ................ 424/93.2, 424/93.1, 93.6; 435/320.1, 325
See application file for complete search history.

(56) References Cited

OTHER PUBLICATIONS

Zeng et al., RS-1 Gene Delivery to an Adult Rs1h Knockout Mouse Model Restores ERG b-Wave with Reversal of the Electronegative Waveform of X-Linked Retinoschisis.Invest Ophthalmol Vis Sci. Sep. 2004;45(9):3279-85.*

Biochemistry John Wiley and Sons, 1990, 126-128.*

Palczewski et al., Ca2+-binding protein in the retina:structure, function and the etiology of human visual diseases BioEssays 22:337-350.*

Blackshaw S, et al., Comprehensive analysis of photoreceptor gene expression and the identification of candidate retinal disease genes. Cell. Nov. 30, 2001;107(5):579-89.*

Mayeur et al., Eight previously unidentified mutations found in the OA1 ocular albinism gene BMC Medical Genetics 2006 1-8.*

Athanasopoulos T, Gene therapy vectors based on adeno-associated virus: characteristics and applications to acquired and inherited diseases (review).Int J Mol Med. Oct. 2000;6(4):363-75.*

Bainbridge JW, et al., Gene therapy progress and prospects: the eye. Aug. 2006;13(16):1191-7. Epub Jul. 13, 2006.*

Cortese et al., "The ocular albinism type 1 (OA1) gene controls melanosome maturation and size." Invest Ophthalmol Vis Sci. 46(12):4358-64 (Dec. 2005).*

Vetrini et al., "The microphthalmia transcription factor (Mitf) controls expression of the ocular albinism type 1 gene: link between melanin synthesis and melanosome biogenesis." Mol Cell Biol. 24(15):6550-9 (Aug. 2004).*

Incerti et al., "Oa1 knock-out: new insights on the pathogenesis of ocular albinism type 1 ." Hum Mol Genet. 9(19):2781-8 (Nov. 22, 2000).*

Voet, Biochemistry John Wiley and Sons, 1990, pp. 126-128.*

Kimchi-Sarfaty C et al., A "silent" polymorphism in the MDR1 gene changes substrate specificity.Science. Jan. 26, 2007;315(5811):525-8.*

Eck et al., 1996, Goodman & Gilman's The Pharmacological Basis of Therapeutics, McGraw-Hill, New York, p. 77-101.*

Brown MD et al., 2001, Gene Delivery with synthetic (non viral) carriers, Int J Pharm, pp. 1-21.*

Gorecki et al., 2001, Prospects and problems of gene therapy: an update, Expert Opin. Emerging Drugs, 6(2): 187-198.*

Enrico Maria Surace et al; Amelioration of Both Functional and Morphological Abnormalities in the Retina of a Mouse Model of Ocular Albinism Following AAV-Mediated Gene Transfer; Molecular Therapy vol. xx; No. xx; Jun. 1, 2005; pp. 1-7.

* cited by examiner

*Primary Examiner*—Maria Leavitt
(74) *Attorney, Agent, or Firm*—Arent Fox LLP

(57) ABSTRACT

There are disclosed methods and compositions for recovering or improving visual function in a mammal, by means of adeno-associated viral vectors suitable for gene delivery to mammalian retina.

6 Claims, 6 Drawing Sheets

SEQUENCE LISTING

<160> NUMBER OF SEQ ID NOS: 7

<210> SEQ ID NO 1
<211> LENGTH: 1275
<212> TYPE: DNA
<213> ORGANISM: Homo sapiens

<400> SEQUENCE: 1

```
atgacccagg caggccggcg gggtcctggc acacccgagc cgcgtccgcg aacacagccc      60
atggcctccc cgcgcctagg gaccttctgc tgccccacgg gggacgcagc cacgcagctc     120
gtgctgagct tccagccgcg ggccttccac gcgctctgcc tgggcagcgg cgggctccgc     180
ttggcgctgg gccttctgca gctgctgccc ggccgccggc ccgcgggccc cgggtccccc     240
gcgacgtccc cgccggcctc ggtccgcatc ctgcgcgctg ccgctgcctg cgaccttctc     300
ggctgcctgg gtatggtgat ccggtccacc gtgtggttag gattcccaaa ttttgttgac     360
agcgtctcgg atatgaacca cacggaaatt tggcctgctg ctttctgcgt ggggagtgcg     420
atgtggatcc agctgttgta cagtgcctgc ttctggtggc tgttttgcta tgcagtggat     480
gcttatctgg tgatccggag atcggcagga ctgagcacca tcctgctgta tcacatcatg     540
gcgtggggcc tggccaccct gctctgtgtg gagggagccg ccatgctcta ctacccttcc     600
gtgtccaggt gtgagcgggg cctggaccac gccatccccc actatgtcac catgtacctg     660
cccctgctgc tggttctcgt ggcgaacccc atcctgttcc aaaagacagt gactgcagtg     720
gcctctttac ttaaaggaag acaaggcatt tacacggaga cgagaggag gatgggagcc     780 gtgatcaaga tccgattttt caaaatcatg ctggttttaa ttatttgttg gttgtcgaat     840
atcatcaatg aaagcctttt attctatctt gagatgcaaa cagatatcaa tggaggttct     900
ttgaaacctg tcagaactgc agccaagacc acatggttta ttatgggaat cctgaatcca     960
gcccagggat ttctcttgtc tttggccttc tacggctgga caggatgcag cctgggtttt    1020
cagtctccca ggaaggagat ccagtgggaa tcactgacca cctcggctgc tgaggggct    1080 cacccatccc cactgatgcc ccatgaaaac cctgcttccg ggaaggtgtc tcaagtgggt    1140
gggcagactt ctgacgaagc cctgagcatg ctgtctgaag ttctgatgc cagcacaatt    1200 gaaattcaca ctgcaagtga atcctgcaac aaaaatgagg gtgaccctgc tctcccaacc    1260
catggagacc tatga                                                     1275
```

<210> SEQ ID NO 2
<211> LENGTH: 1218
<212> TYPE: DNA
<213> ORGANISM: Mus musculus

<400> SEQUENCE: 2

```
atggcctccc cgcgcctggg aattttctgc tgccctacgt gggacgcagc cacacagctg      60
gtgctaagct tccaaccgcg ggtgttccat gccctgtgcc tgggaagcgg cactctccgc     120
ctggtgcttg gcctccttca gctcctatca gggcgtcgat ctgttggtca cagggcgcct     180
gcgacatccc cagccgcctc agtccacatc ctccgtgctg ccactgcctg tgacttgctt     240
ggctgcctgg gaatcgttat caggtccaca gtgtggatag cctacccaga gttcattgaa     300
aacatttcca atgtgaatgc aacagacatt tggcctgcta ctttctgtgt ggggagcgca     360
atgtggatcc agctgttgta cagtgcctgc ttctggtggc tcttttgcta tgcagttgat     420
gtatacttgg tgatcaggag atcggcggga cggagcacca tcctgctgta ccacatcatg     480
gcctggggcc tggctgtgct gctctgtgtg gagggagcag tcagtctcta ctacccttct     540
gtgtccaggt gtgagagggg cctggaccat gccatccccc attatgtcac cacatacttg     600
ccacttctgc ttgtcttggt ggccaaccca atcctgttac acaagacagt gacttcagtg     660
gcctctttac tgaaaggaag aaaaggtgtt tacacagaga tgagagact gatggggct     720 gtgatcaaga cccgtttttt caaaataatg ctggtgttaa ttgcatgttg gttgtccaat    780
atcatcaatg aaagtctttt gttctacctt gaaatgcaac cagatatcca tggaggctct    840
```

```
ctgaaacgca tcctgaatgc agctaggacc acatggttta taatgggaat actgaatcca    900
gcccaaggac ttctcttgtc tctggccttc tatggctgga caggatgcag cctggatgtc    960
catcctccca agatggtgat tcagtgggaa acaatgactg cctctgctgc tgagggcacg   1020
taccagaccc ctgtgcgttc ctgtgtgccc catcaaaacc ccaggaaggt tgtatgtgtc   1080
gggggacata cttctgatga ggtgctgagc attttgtctg aagattcaga tgccagtact   1140
gttgaaatcc atactgcaac tgggtcctgc aacataaagg aagttgactc catttcccaa   1200
gcccaggggg aactctga                                                 1218

<210> SEQ ID NO 3
<211> LENGTH: 595
<212> TYPE: DNA
<213> ORGANISM: Cytomegalovirus

<400> SEQUENCE: 3
aagctagcta gttattaata gtaatcaatt acggggtcat tagttcatag cccatatatg     60
gagttccgcg ttacataact tacggtaaat ggcccgcctg gctgaccgcc caacgacccc    120
cgcccattga cgtcaataat gacgtatgtt cccatagtaa cgccaatagg gactttccat    180
tgacgtcaat gggtggagta tttacggtaa actgcccact tggcagtaca tcaagtgtat    240
catatgccaa gtacgccccc tattgacgtc aatgacggta aatggcccgc ctggcattat    300
gcccagtaca tgaccttatg ggactttcct acttggcagt acatctacgt attagtcatc    360
gctattacca tggtgatgcg gttttggcag tacatcaatg ggcgtggata gcggtttgac    420
tcacggggat ttccaagtct ccaccccatt gacgtcaatg ggagtttgtt ttggcaccaa    480
aatcaacggg actttccaaa atgtcgtaac aactccgccc cattgacgca aatgggcggt    540
aggcgtgtac ggtgggaggt ctatataagc agagctggtt tagtgaaccg tcaga         595

<210> SEQ ID NO 4
<211> LENGTH: 668
<212> TYPE: DNA
<213> ORGANISM: Homo sapiens

<400> SEQUENCE: 4
ccatgttgcc cacgctggtc tccaactctt gagctcaagc gatctgcctg cctcggcctc     60
ccaaggtgct gggattacag gtgtgagcta ctgctctttc tttaacattg atctgtttgt    120
ttcattcatt aattgtaaac gaaaatcctg cctctgtggg attatatcca tgaatgagag    180
aggccataaa aaaagcact aattggacaa ccatctctac ttaggaaaaa agcagttaca    240
gggatcagtc acagtttatg aacatgttct ggcgccttaa aggcatcaaa atcaggatgt    300
cagagtccca ataggaaag atctagtcca cgaggcctgt ttctctagaa gaccagtaaa    360
gatggcaggt ttggcgctct aggtggcaga gaaaccacca ggaaggcttg gtgaatgggg    420
agaaaggtaa ccttcccaac cttctgctt ctccttccac ttccctcctc ctcctccctc    480
ttcctctcct ctcagccctc cctctctctg tcctcctcct ccgccgccc aagcatcacc    540 tcgtgaggcc tcgtggcgtt agcccagtgc tctcggcccc caccgagcct ggctctactg    600
caggcgctgg ggtttgggt ggggagagg cccagggcac atgatgccgc ccccagcccg    660
cccagcac                                                            668

<210> SEQ ID NO 5
<211> LENGTH: 1465
<212> TYPE: DNA
```

<213> ORGANISM: Homo sapiens

<400> SEQUENCE: 5

```
ttttaatgtg gaaagataga tattaatctc ctcttctatt actctccaag atccaacaaa      60
agtgattata ccccccaaaa tatgatggta gtatcttata ctaccatcat tttataggca     120
tagggctctt agctgcaaat aatggaacta actctaataa agcagaacgc aaatattgta     180
aatattagag agctaacaat ctctgggatg gctaaaggat ggagcttgga ggctacccag     240
ccagtaacaa tattccgggc tccactgttg aatggagaca ctacaactgc cttggatggg     300
cagagatatt atgatgcta agccccaggt gctaccatta ggacttctac cactgtccct      360
aacgggtgga gcccatcaca tgcctatgcc ctcactgtaa ggaaatgaag ctactgttgt     420
atatcttggg aagcacttgg attaattgtt atacagtttt gttgaagaag accctaggg      480
taagtagcca taactgcaca ctaaatttaa aattgttaat gagtttctca aaaaaaatgt     540
taaggttgtt agctggtata gtatatatct tgcctgtttt ccaaggactt ctttgggcag     600
taccttgtct gtgctggcaa gcaactgaga cttaatgaaa gagtattgga gatatgaatg     660
aattgatgct gtatactctc agagtgccaa acatatacca atggacaaga aggtgaggca     720
gagagcagac aggcattagt gacaagcaaa gatatgcaga atttcattct cagcaaatca     780
aaagtcctca acctggttgg aagaatattg gcactgaatg gtatcaataa ggttgctaga     840
gagggttaga ggtgcacaat gtgcttccat aacattttat acttctccaa tcttagcact     900
gatctgtgaa gacagggaca gggacaatac ccatctctgt ctggttcata ggtggtatgt     960
aatagatatt tttaaaaata agtgagttaa tgaatgaggg tgagaatgaa ggcacagagg    1020
tattaggggg aggtgggccc cagagaatgg tgccaaggtc cagtggggtg actgggatca    1080
gctcaggcct gacgctggcc actcccacct agctcctttc tttctaatct gttctcattc    1140
tccttgggaa ggattgaggt ctctggaaaa cagccaaaca actgttatgg gaacagcaag    1200
cccaaataaa gccaagcatc aggggatct gagagctgaa agcaacttct gttccccctc     1260
cctcagctga aggggtgggg aagggctccc aaagccataa ctccttttaa gggatttaga    1320
aggcataaaa aggcccctgg ctgagaactt ccttcttcat tctgcagttg gtgccagaac    1380
tctggatcct gaactggaag aaaatgtcta tccagtaagt atctctggga gactttttta    1440
aaacaccttc atggattcat gataa                                          1465
```

<210> SEQ ID NO 6
<211> LENGTH: 86
<212> TYPE: DNA
<213> ORGANISM: Artificial Sequence
<220> FEATURE:
<223> OTHER INFORMATION: Description of Artificial Sequence: Synthetic primer

<400> SEQUENCE: 6

```
aagcggccgc atggcctccc cgcgcctggg aattttctgc tgccctacgt gggacgcagc      60
cacacagctg gtgctaagtt tccaac                                           86
```

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: Synthetic primer -continued

```
<400> SEQUENCE: 7
ttgactccat ttcccaagcc caggggggaac tctgaaagct taa          43
```

METHODS AND COMPOSITIONS FOR RECOVERING OR IMPROVING VISUAL FUNCTION

The invention provides methods and compositions for recovering or improving visual functions, e.g. by treating ocular conditions and diseases that impair eye functionality. More particularly, the invention provides a method for gene delivery to mammalian retina by means of adeno-associated viral vectors. In a preferred embodiment, the invention provides genetic constructs and adeno-associated viral vectors for the transfer of Oa1 gene to the retina of patients affected by ocular albinism type I.

BACKGROUND OF THE INVENTION

Congenital hypopigmentary diseases ("albinism") result from a defect in the synthesis or distribution of melanin pigment [1]. Melanin is responsible for skin, hair, and eye pigmentation. It is synthesized from the amino acid tyrosine in special organelles, the melanosomes. Different forms of albinism are due to mutations in genes involved in melanin production and accumulation [2]. Ocular albinism (OA) affects primarily the eye; oculocutaneous albinism (OCA) affects the skin and hair in addition [1].

Ocular Albinism Type I (OA1; MIM 300500) is the most common OA form [1]. OA1 is transmitted as an X-linked trait, with affected males showing the complete phenotype and heterozygous carrier females showing only minor signs of the disease. Visual abnormalities in OA1 are similar to those present in all forms of albinism [1, 3]. OA1 male patients have reduced visual acuity, which represents a major handicap, nystagmus, strabismus and marked photophobia [1]. This results from a developmental disorder of the retina characterized by foveal hypoplasia and misrouting of the optic fibers at the chiasm [3]. In addition, unlike other forms of albinism, the OA1 retinal pigment epithelium (RPE) and, to a lesser extent, the skin melanocytes present with characteristic large pigment granules, the macromelanosomes, suggesting that abnormal melanosomal biogenesis might occur in OA1 [4-6].

The gene responsible for OA1 (OA1) has been identified by positional cloning [7]. It encodes an orphan G-protein coupled receptor (OA1), which crosses the melanosomal membrane. Oa1 is expressed exclusively in RPE and skin melanocytes [8-12] and its transcript is detectable in murine embryonic RPE since early stages of development [10].

Gene transfer holds great promises for the treatment of inherited retinal diseases [16, 17]. Vectors based on adeno-associated viruses (AAV) are able to stably and efficiently transduce the retina of animal models of retinal diseases and their toxicity and efficacy will be soon evaluated in the human retina [18-20]. It has been shown that AAV vectors with an AAV1 capsid (AAV2/1) efficiently transduce the murine RPE [21-23], thus representing important tools for the treatment of animal models of RPE defects, such as Oa1−/− mouse.

Retinal electrophysiological function has been analyzed in albino (OCA) rodents and abnormalities in both light-evoked responses and ability to recover from photoreceptor desensitization following bright light exposure (dark adaptation) have been described [24-27].

DESCRIPTION OF THE INVENTION

In one aspect, the invention provides a method for recovering or improving visual function in a mammalian subject, which comprises:

a) providing a recombinant adeno-associated viral (AAV) vector carrying an expression cassette which contains a nucleic acid molecule encoding Oa1 or a protein substantially homologous to Oa1, wherein said nucleic acid molecule is operably linked to regulatory control elements that direct the transcription and translation thereof;

b) transducing retinal pigment epithelial cells with said recombinant AAV vector, whereby said nucleic acid molecule is expressed by the retinal pigment epithelial cells at a level sufficient to recover or improve visual function in said mammalian subject.

As a result of this treatment, the number of melanosomes in retinal pigment epithelial cells is increased and the dark adaptation of the treated subject is improved.

In a particularly preferred embodiment of the invention, the above method is applied to human subjects who have been positively diagnosed for the Nettleship-Falls Disease (Ocular Albinism Type I).

Recombinant adeno-associated viral (AAV) vectors are known to be safe and efficient vehicles for gene transfer. Several serotypes of AAV have so far been isolated and vectors based on them have been constructed and used for gene-therapy protocols in animal models. Various AAV serotypes may be used according to the invention, depending e.g. on their level of transgene expression and on the presence of pre-existing serotype-specific antibodies in the patient to be treated, which may limit the efficiency of infection. AAV vectors of serotype 1, 2, 4 or 6 are preferred.

The OA1 gene (GenBank acc. no.: NM000273), also known as GPR143, is located in Xp22.3 and encodes an orphan G-protein coupled receptor, which crosses the melanosomal membrane. Oa1 is expressed exclusively in the retinal pigment epithelium (RPE) and skin melanocytes, and its transcript is detectable in murine embryonic RPE from early stages of development. For the purpose of this invention, the coding sequence of Oa1 (human and murine sequences deposited at GenBank NM_00027 and NM_010951, respectively), or a sequence substantially homologous thereto, is functionally linked to a promoter able to regulate the expression of the transgene in a eukaryotic cell, preferably in a mammalian retinal cell, more preferably in a retinal pigment epithelium cell. Suitable promoters that can be used according to the invention include the RPE65, the Oa1 and the ubiquitous cytomegalovirus (CMV) promoters, as well as inducible promoters.

In a particularly preferred embodiment of the invention, the expression cassette contains the human or mouse Oa1 coding sequence (SEQ ID No: 1 and SEQ ID No: 2, respectively) functionally linked to a promoter sequence which is selected from the group consisting of the CMV promoter (SEQ ID No: 3), the human OA1 promoter (SEQ ID No: 4; −668 bp from the atg of OA1 coding sequence, GenBank AC003047) and the human RPE65-specific promoter fragment (SEQ ID No: 5; 806 bp, GenBank NM_000329).

The construction of an AAV vector can be carried out following procedures and using techniques which are known to any person skilled in the art. The theory and practice for adeno-associated viral vector construction and use in therapy are illustrated in several scientific and patent publications (the following bibliography is herein incorporated by reference: Flotte T R. Adeno-associated virus-based gene therapy for inherited disorders. Pediatr Res. 2005 December; 58(6):1143-7; Goncalves M A. Adeno-associated virus: from defective virus to effective vector, Virol J. 2005 May 6; 2:43; Surace E M, Auricchio A. Adeno-associated viral vectors for retinal gene transfer. Prog Retin Eye Res. 2003 November;

22(6):705-19; Mandel R J, Manfredsson F P, Foust K D, Rising A, Reimsnider S, Nash K, Burger C. Recombinant adeno-associated viral vectors as therapeutic agents to treat neurological disorders. Mol Ther. 2006 March; 13(3):463-83.).

In a further aspect, the invention relates to a pharmaceutical composition containing an AAV vector expressing the Oa1 coding sequence, in a form suitable for ocular administration. Suitable administration forms include, but are not limited to, injectable solutions or suspensions, eye lotions and ophthalmic ointment. In a preferred embodiment, the AAV vector is administered by subretinal injection, e.g. by injection in the vitreous, in the anterior chamber or in the retrobulbar space. Preferably the viral vectors are delivered via a transcleral transchorodial approach (as described in Liang, F. Q. et al., Intraocular delivery of recombinant virus. Methods Mol. Med. 47: 125-139).

The doses of virus for use in therapy shall be determined on a case by case basis, depending on the administration route, the severity of the disease, the general conditions of the patients, and other clinical parameters. In general, suitable dosages will vary from $10^9$ to $10^{12}$ vg (vector genomes)/ml.

DETAILED DESCRIPTION OF THE INVENTION

A mouse knock-out (KO) model has been generated which shows some of the OA1 landmarks [13]. The Oa1 –/y male or –/– female mice (herein referred to as Oa1–/– mice) are viable and fertile. Ophthalmologic examination shows hypopigmentation of the ocular fundus in mutant animals compared with wild-type [13]. Microscopic examination of the RPE shows the presence of macromelanosomes already detectable at birth (P1) and comparable with those described in OA1 patients [13]. In addition, Oa1–/– mice (similarly to the OA1 patients) show abnormal crossing of the optic fibers at the chiasm which occurs between embryonic days 12 and 18 in mice [13-15]. Foveal hypoplasia can not be evaluated in rodents who lack this structure. The Oa1 mouse KO represents a unique model for the elucidation of the OA pathophysiology and for testing potential therapies for an otherwise untreatable ocular disorder.

To test whether Oa1 gene knock-out results in abnormal retinal function, extensive electophysiological analysis was performed in Oa1–/– and wild type, age-matched C57/BL6 mice. Ganzfeld flash electroretinograms (ERG) were measured after 3 hour dark adaptation in Oa1–/– and wild-type mice (8-9 months old, FIG. 1). The amplitude of ERG a—(FIG. 1B,C) and b—(FIG. 1B,D) waves is significantly decreased in Oa1–/– mice when compared to wild type C57/BL6 mice, suggesting abnormal photoreceptor function as a result of absence of the Oa1 gene. Compared to the scotopic responses, photopic ERG was affected to a lesser extent (statistical significance among the Oa1–/– and wild type animals was not reached using the ANOVA test described in Material and Methods) suggesting that absence of Oa1 impairs mainly the rod pathway. A similar shift towards lower intensities has been recently observed in other albino mice [24, 25, 27]. These combined results suggest that the RPE defect in albinism, whether due to absence of melanin or to abnormal melanosomal biogenesis, impacts on photoreceptor function as assessed by flash ERG analysis.

The ability of the Oa1–/– mouse retina to recover from a photoreceptor desensitizing light stimulus (dark adapt), which has been reported to be delayed in rodents affected by different types of albinism [25-27], was then analyzed. The mice were exposed to an intense bleaching condition (600 cd*m-2 for 3 min) before monitoring the recovery of b-wave using a flash of 1 cd*m-2 sec-1. Recovery of b-wave amplitude was measured over time; the amplitude of the b-wave relative to that prior to photoreceptor desensitization is represented in FIG. 1E while absolute values are depicted in table 1. A significant delay in recovery from photoreceptor desensitization was observed in Oa1–/– mice when compared to wild type mice. The Oa1–/– mice b-wave eventually recovers 100'-120' after bleaching conditions suggesting that prolonged functional uncoupling between the RPE and the photoreceptors may result as a consequence of the absence of Oa1.

An AAV2/1 vector expressing the murine Oa1 coding sequence under the control of the ubiquitous cytomegalovirus (CMV) promoter (AAV2/1-CMV-mOa1) was produced and injected subretinally in 1 month-old Oa1–/– mice. Four weeks later Oa1 expression was analyzed in retinal sections by immunofluorescence: a strong signal was detected in both RPE and photoreceptors.

To test whether the Oa1-mouse photoreceptor dysfunction is reversible, Oa1–/– mice (8 months old) were subretinally injected in one eye with $2-3 \times 10^9$ genome copies (GC) of a 1:1 mixture of AAV2/1-CMV-mOa1+AAV2/1-CMV-EGFP (expressing the enhanced green fluorescence protein, EGFP) and in the contralateral with the same dose of AAV2/1-CMV-EGFP alone as control. Four weeks after vector administration, indirect ophthalmoscopic evaluation was performed to assess EGFP expression [21] followed by flash ERG analysis (FIG. 2). b-wave amplitude elicited in photopic conditions was higher (albeit not statistically significant) in Oa1-treated than untreated mice suggesting a partial rescue of cone function. In addition, both a- and b-waves amplitude in scotopic conditions were significantly higher (albeit not normal) at the highest light intensities in the retinae injected with both the Oa1 and EGFP vectors than in the contralateral injected with the vector expressing EGFP alone (FIG. 2).

These data suggest that a partial rescue of both rod and cone function occurred in the retinae expressing recombinant Oa1. Although AAV-mediated Oa1 expression was detected in both RPE and photoreceptors, the recovery of photoreceptors activity in the Oa1–/– mouse is likely due to robust transduction of the RPE which is the only Oa1 physiological site of expression in the retina (and therefore affected in the KO animal).

To verify whether the delayed recovery from photoreceptor desensitization present in the Oa1–/– mice was reversible and whether this could be dependent on the age of the animals treated, 2 cohorts of Oa1–/–mice of different ages (1 and 8 months old) were subretinally injected similarly to those treated in FIG. 2 and four weeks later their ability to dark adapt tested (FIG. 3). Independently of the age of treatment, the retinae that received the Oa1 vector completely recovered from the delay in dark adaptation in 75' similarly to wild type retinae. The contralateral EGFP-treated retinae do not recover after 90', the latest time point of the analysis in some animals. This suggests that Oa1 gene delivery, applied at different time points to the adult retina, can rescue the delayed dark adaptation present in the mouse model.

To test whether the modification in electrophysiological activity following gene transfer to the Oa1–/– mouse retina could be related to changes occurring in the Oa1––/– RPE melanosomes, which are of lower number (Marigo et al, unpublished results) and increased size since birth [13], eyes from some of the animals used for the experiment depicted in FIG. 3A were enucleated and the transduced, EGFP-positive areas from eyes injected either with the AAV2/1-CMV-mOa1+AAV2/1-CMV-EGFP mixture or with the AAV2/1-CMV-EGFP vector alone were dissected under a fluorescent microscope. EGFP-positive, transduced areas accounted for 40-50% of the whole retina with minor inter-animal variation. Two different regions of the eye were analyzed, one centrally located in the proximity of the optic nerve and the remaining peripheral region, representing the vast majority of the retina. The RPE from these regions was isolated and analyzed by electron microscopy to assess melanosome number and size.

A representative picture from Oa1- or EGFP-injected eyes is shown in FIG. 4. In two independent electron microscopy measurements, the melanosome density (melanosome/$\mu m^2$) in the peripheral RPE injected with the Oa1-expressing vector was higher than that measured in the same area of the contralateral eyes injected with the EGFP vector alone (FIG. 5A). In one eye, both the transduced peripheral and central retinae were analyzed, confirming that treatment with the Oa1 vector increases melanosome density independently of the area of transduction (FIG. 5B). The number of normal sized melanosomes in the peripheral RPE is increased in the 2 retinae treated with the Oa1 vector when compared to the contralateral treated with the EGFP vector alone, while the number of giant size melanosomes (>1.5 $\mu m$) remained similar (FIG. 5C). This suggests that in the period following gene transfer (4 weeks) biogenesis of melanosomes of normal size occurs in the Oa1–/– RPE treated with the therapeutic vector rather than modification of the pre-existing abnormal organelles.

The results show that gene transfer to the adult retina can rescue the electrophysiological abnormalities, as well as the altered melanosome density observed in Oa1–/– mice.

$n=10$ eyes) are shown. The amplitude of a- and b-wave elicited in photopic conditions is indicated by an arrow. E) Recovery of b-wave amplitude after bleaching condition (600 cd*$m^{-2}$ for 3 min) in Oa1–/– (empty triangles, n=12 eyes) and wild type C57/BL6 mice (black circles, n=12 eyes). The amplitude of b-wave after bleaching condition was measured for flash of 1 cd*$m^{-2} sec^{-1}$ and expressed as relative mean value compared to the amplitude of b-wave measured before bleaching condition. Asterisks depict statistical significance ($p<0.05$).

FIG. 2. Partial recovery of the rod function following subretinal delivery of AAV2/1-CMV-Oa1 to Oa1–/– mice. Amplitude of a- (A) and b-waves (B) in scotopic and photopic (depicted by the arrows) conditions (mean±S.E.M) from AAV2/1-CMV-Oa1 (empty triangles, n=5) and AAV2/1-CMV-EGFP (black circles, n=3) treated eyes recorded 1 month after vector delivery. Asterisks depict statistical significance ($p<0.05$).

FIG. 3. Rescue from delayed recovery from photoreceptor desensitization in Oa1–/– mice treated with AAV. Progressive recovery over time of the b-wave amplitude following bleaching conditions in 2-(A) and 9-month (B) old Oa1–/– animals injected subretinally either with AAV2/1-CMV-Oa1 (black circles, n=6 eyes in both A and B) or AAV2/1-CMV-EGFP (empty triangles, n=6 eyes in A and 9 in B). Asterisks depict statistical significance ($p<0.05$).

FIG. 4. Increased density of normal sized stage IV melanosomes in the Oa1 retinae transduced with AAV. Representa-

| C57/BL6 | | | | C57/BL6 Oa1 –/– | | |
|---|---|---|---|---|---|---|
| MEAN "B" WAVE($\mu V$) | STD. DEV. | STD. ERR. | TIME (min) | MEAN "B" WAVE ($\mu V$) | STD. DEV. | STD. ERR. |
| 201.3201 | 72.16918313 | 22.82189956 | –4 | 119.3180833 | 58.16576671 | 16.79101053 |
| 24.7725 | 16.57714234 | 5.242152688 | 0 | 12.79395 | 7.750638312 | 2.450967039 |
| 48.0427 | 26.40620808 | 8.350376191 | 5 | 27.2946 | 15.88910123 | 5.024574985 |
| 70.2866 | 69.77704883 | 22.06544027 | 15 | 37.4196 | 27.44337372 | 8.678356765 |
| 115.6165 | 95.11824733 | 30.07903086 | 30 | 49.0226 | 31.59256886 | 9.990447472 |
| 138.601 | 83.33688361 | 26.35343653 | 45 | 62.1566 | 34.21601797 | 10.82005493 |
| 180.1548 | 87.90791193 | 27.7989226 | 60 | 75.6743 | 43.81319146 | 13.85494766 |
| 191.8519 | 88.42408257 | 27.96215009 | 75 | 80.1195 | 31.17113631 | 12.72556311 |

The non-progressive nature of the disease and the possibility to ameliorate visual function with treatment to the adult retina open novel therapeutic perspectives for albino patients.

Table 1. Values of mean b-wave amplitudes—including standard deviation and error—at different time points before (–4') and after photoreceptor desensitization.

ERG components in scotopic and photopic conditions: a- (C) and b-waves (D) in Oa1–/– and C57/BL6 wild type mice. The amplitudes (mean±S.E.M.) evoked by increasing light intensities in scotopic conditions in Oa1–/– mice (empty triangles, n=10 eyes) and age matched controls (black circles, tive electron micrographs of peripheral RPE in 2-months old treated and control Oa1–/– retinae. Left panel shows the low melanosome density and macromelanosome presence typical of the Oa1-RPE transduced with AAV2/1-CMV-EGFP. Middle and right panels show different areas of the same RPE cell in a retina transduced with AAV2/1-CMV-Oa1. Note the increased number of normal sized melanosomes (middle panel) with persistence of macromelanosomes (right panel). Size bar 1.5 $\mu m$.

Figure 1:
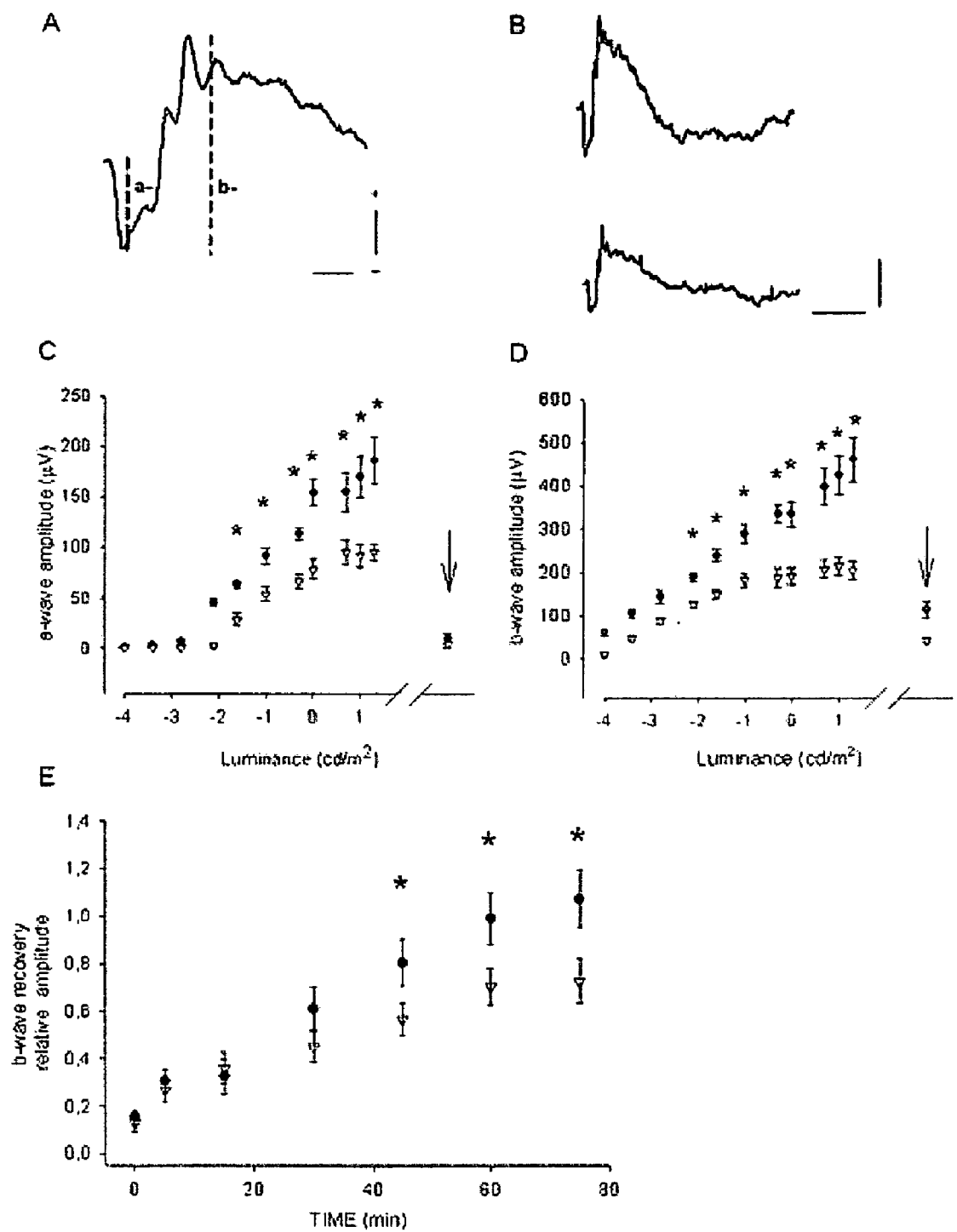
FIG. 1. Electrophysiological abnormalities in Oa1 mice. ERGs recorded after dark adaptation. A) Typical ERG produced by a flash (10 cd*m-2) in a dark adapted wild type C57/BL6 mouse: a- and b-waves are indicated in an expanded scale (horizontal bar=20 msec, vertical bar=150 $\mu V$). Dotted lines refer to a- and b-wave amplitudes. B) ERG produced by a flash (1 cd*$m^{-2}$) in a wild type C57/BL6 (upper waveform) and Oa1–/– (lower waveform) mouse; horizontal bar=100 msec, vertical bar=200 $\mu V$.
Figure 2:
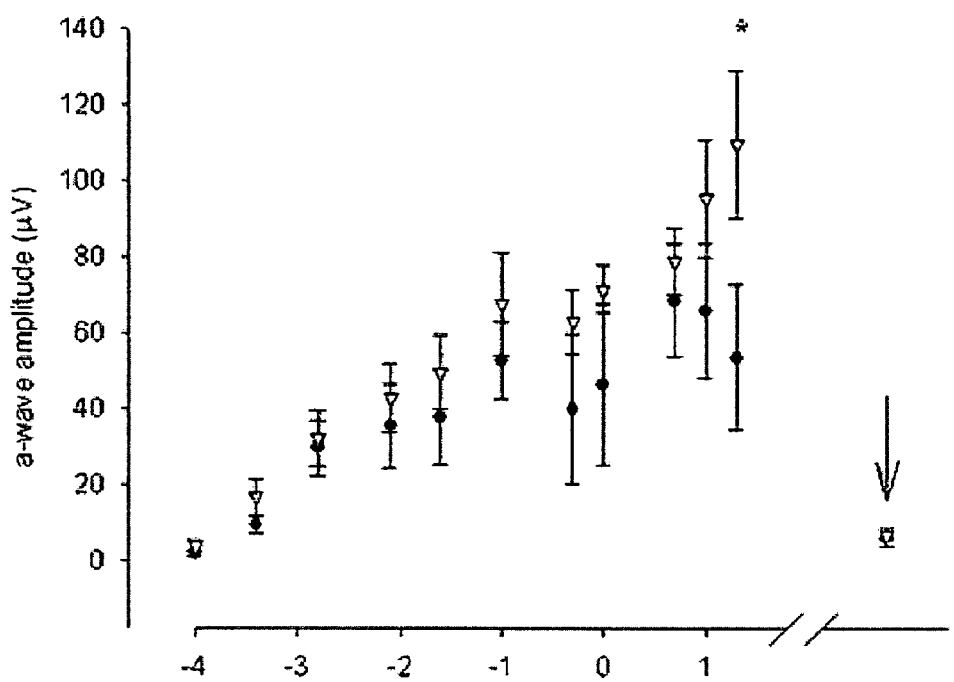
Figure 2:
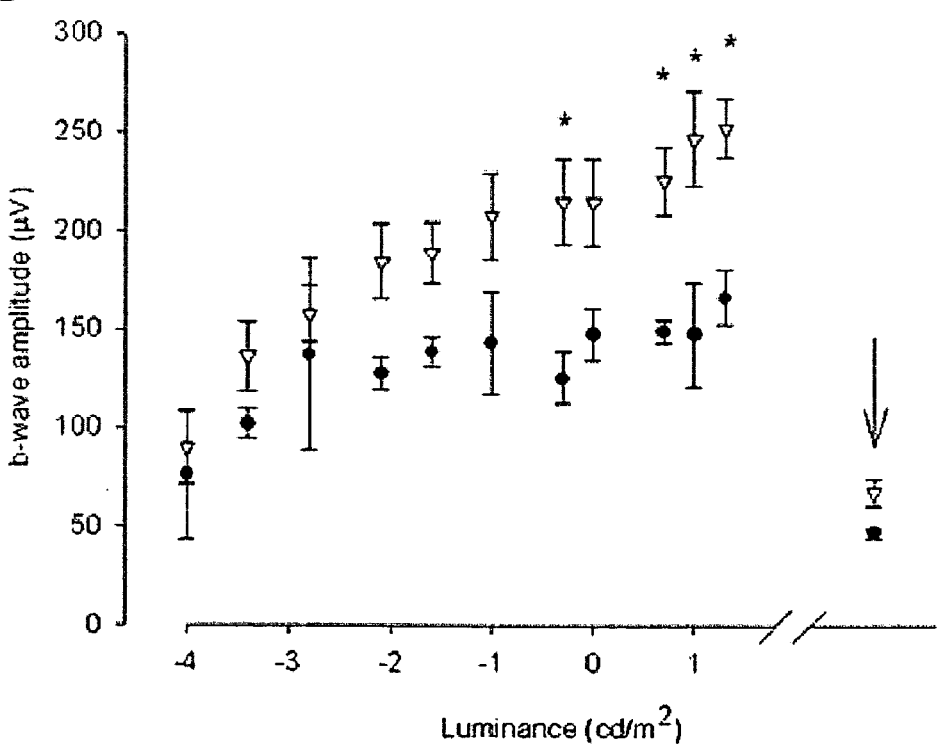
Figure 3:
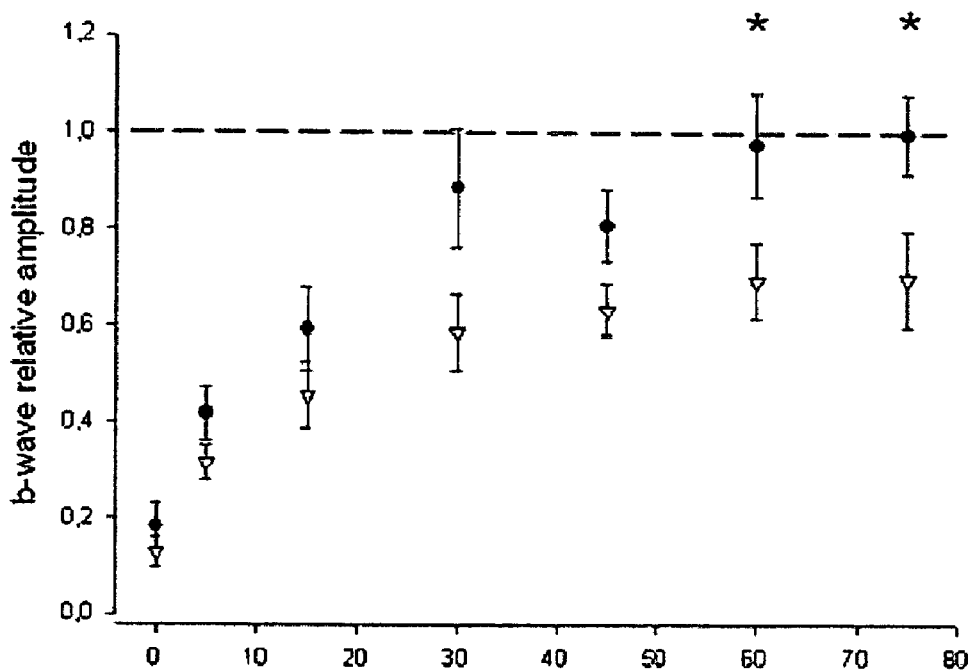
Figure 3:
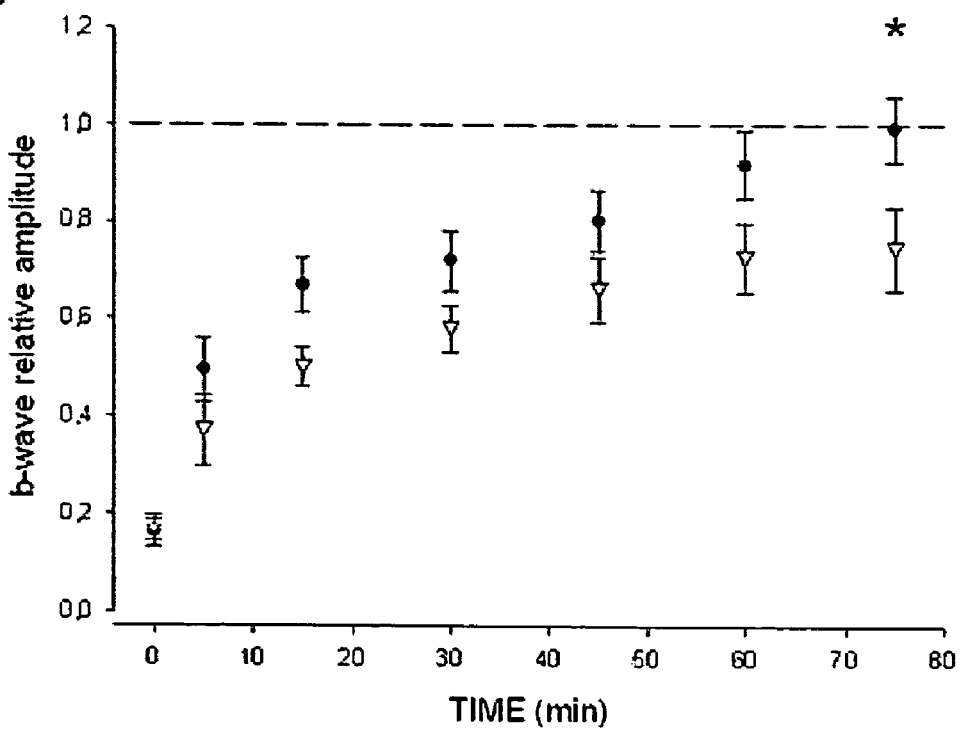
Figure 4:
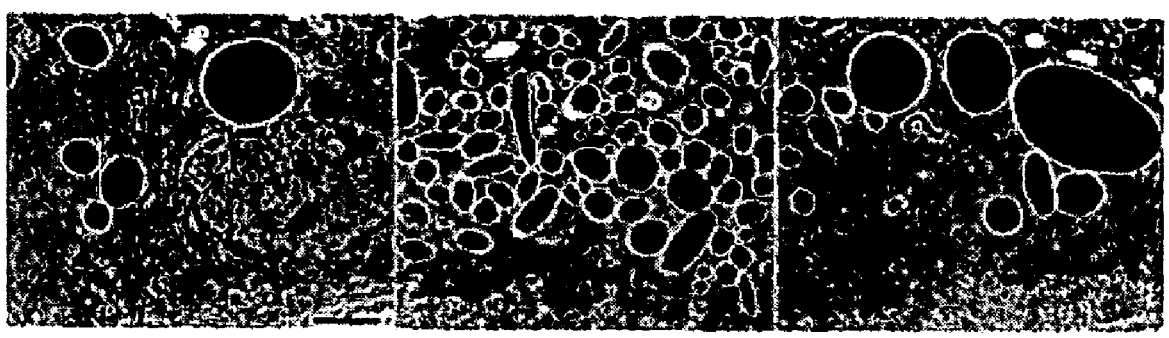
Figure 5:
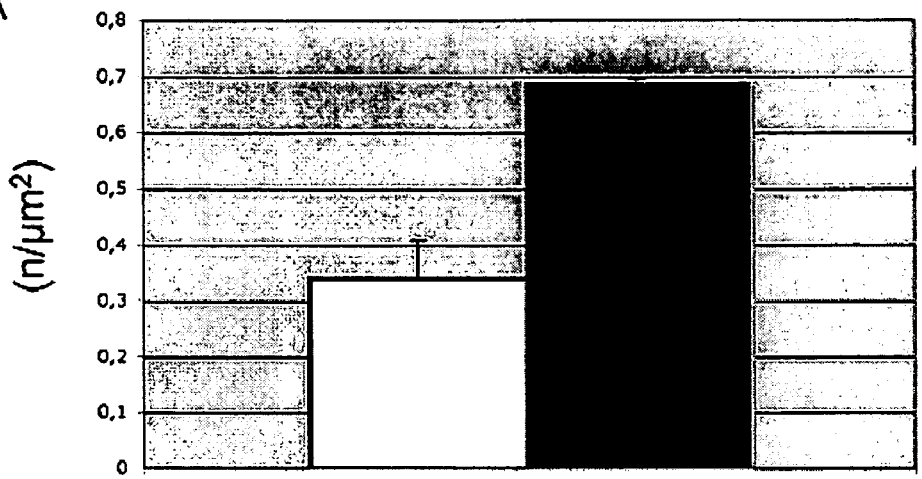
Figure 5:
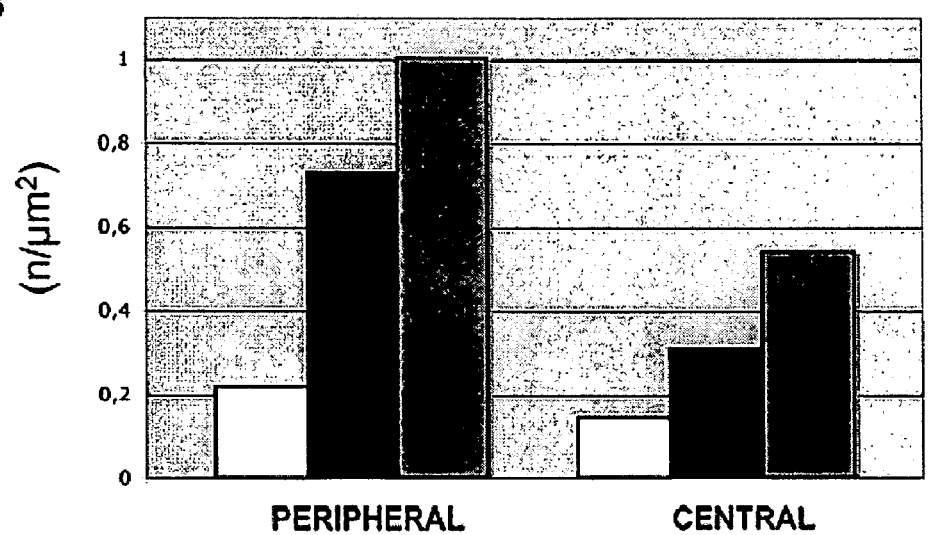
Figure 5:
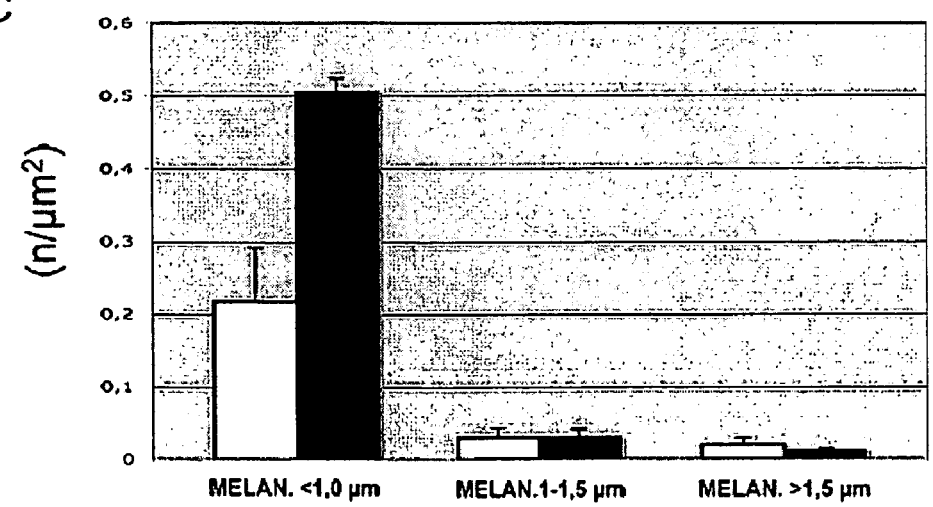

FIG. 5. Melanosomal modifications in the Oa1–/– RPE following delivery of AAV2/1-CMV-Oa1 (black bar) or AAV2/1-CMV-EGFP (white bar).

A) Mature (stage IV) melanosome density in the peripheral RPE (mean±S.E.M.; n=2 eyes/group, 2 sections/eye). B) Mature (stage IV) melanosomal density in the peripheral and central RPE area of AAV-treated and wild type C57/BL6 (grey bar) retinae (n=1 eye/group, mean of 2 sections/area). C) Density of different size melanosomes in the peripheral RPE transduced with AAV (mean±S.E.M.; n=2 eyes/group, 2 sections/eye). Melan, melanosome size.

Figure 6:
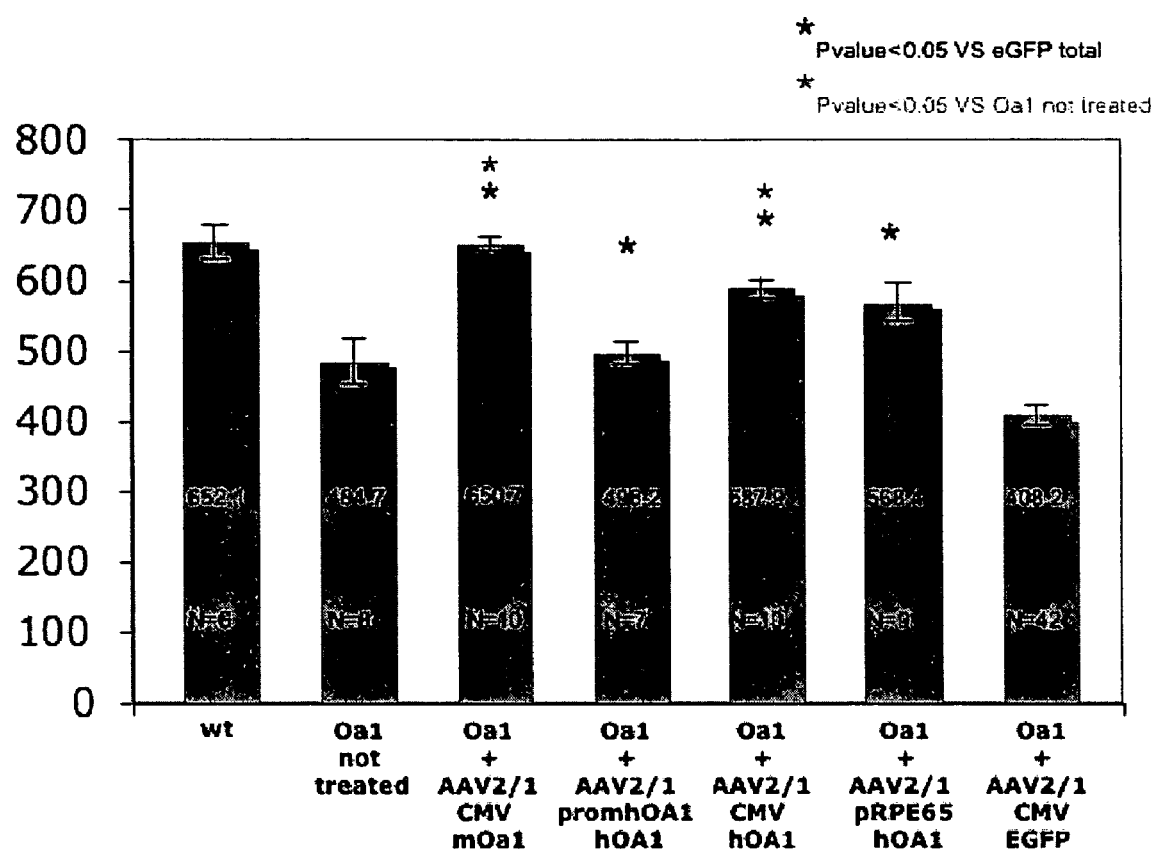

FIG. 6. Recovery of retinal function following subretinal delivery of AAV2/1 vectors encoding Human or mouse Oa1 gene under the transcriptional control of CMV, Oa1, and RPE65 promoters. Max B-wave amplitude (mean±SEM) produced by a flash (10 cd m-2) in dark adapted wt, Oa1 and treated animals. Treated animals were injected with AAV2/1 viruses encoding human or mouse Oa1 under different promoters. Asterisks depict statistical significance (P<0.05): gray is significance vs Oa1 not treated mice; black is significance vs Oa1 mice injected with AAV2/1 CMV eGFP as control. mOa1, mouse Oa1 coding sequence; hOA1, human OA1 coding sequence; promhOA1, human OA1 promoter fragment; pRPE65, human RPE65 promoter fragment.

MATERIAL AND METHODS

Generation of the pAAV2.1-CMV-Oa1 construct, AAV vector production, and purification. The murine Oa1 coding sequence in pBS-SK plasmid was mutagenized via PCR using the Advantage cDNA PCR Kit (Clontech, Palo Alto, Calif., USA) in order to eliminate the HindIII restriction site, and to insert a Not and a HindIII sites at the 5' and 3' end respectively with the following primers: Oa1-NotI-F: AAGCGGCCGCATGGCCTCCCCGCGC-CTGGGAATTTTCTGCTGCC CTACGTGGGACGCAGC-CACACAGCTGGTGCTAAGUTCCAAC (SEQ ID NO: 6); Oa1-HindIII-R: TTGACTCCATTTCCCAAGC-CCAGGGGGAACTCTGAAAGCTTAA (SEQ ID NO: 7). The PCR product was then digested NotI, HindIII and cloned in pAAV2.1-CMV-EGFP [28] by removing the EGFP coding sequence (NotI-HindIII). AAV2/1-CMV-Oa1 and AAV2/1-CMV-EGFP vectors were produced by triple transfection, purified by CsCl2 ultracentrifugation and titered using a real-time PCR-based assay as previously described [21, 28]. AAV vectors were produced by the AAV TIGEM Vector Core.

Subretinal vector administration. All procedures on mice (including their euthanasia) were performed in accordance with institutional guidelines for animal research. Oa1 (kept in a C57/BL6) and wild type C57/BL6 mice were used (Charles River Italia, Lecco, Italy). For subretinal vector administration, mice were anesthetized with an intraperitoneal injection of avertin at 2 ml/100 g body weight (1.25% (w/v) 2,2,2-tribromoethanol and 2.5% (v/v) 2-methyl-2-butanol; Aldrich, St. Louis, Mo., USA) and viral vectors were delivered via a transscleral transchoroidal approach as described [29].

Immunofluorescence. One month after injection treated and control eyes were collected, fixed overnight in 4% paraformaldehyde, incubated in 30% sucrose for 2 hours and then frozen in OCT compound (Kaltech, Padova, Italy). Serial cryosections (12 μm thick) were obtained. To detect Oa1 by immunofluorescence, cryosections were fixed in 4% paraformaldehyde for 20'. To detect Oa1 by immunofluorescence, cryosections were fixed in 4% paraformaldehyde for 20', washed and incubated at room temperature in 30 mM $NH_4Cl$ for 30'. Sections were then permeabilized and blocked against non-specific binding in a buffer containing 10% FBS (GIBCO, Invitrogen Life Technology, Carlsbad, Calif.), 0.1% Saponin in PBS over night at 4° C. Samples were then washed with PBS and incubated with rabbit anti-mouse-Oa1 primary antibody (1:50 diluted in 0.01% saponin) for two hours at room temperature. After extensive washing in 0.01% saponin, sections were incubated with secondary Cy2-labeled anti-rabbit antibody (Jackson Immunoresearch, Cambridgeshire, UK, 1:100 diluted in 0.01% saponin) for 1 hour at room temperature, washed with PBS and mounted with Vectashield mounting media (Vector Laboratories, Burlingame, Calif.). Treated slides were then analyzed under the Axioplan 2 Imaging fluorescent microscope (Carl Zeiss, Milano, Italy).

Electrophysiological recordings. Flash ERG was evoked by 10 msec flashes of light generated through a Ganzfeld stimulator (Lace, Pisa, Italy). The electrophysiological signals were recorded through gold plate electrodes inserted under the lower eyelids in contact with the cornea previously anaesthetized with ossibuprocaine (Novesine, Novartis Pharma, Switzerland). Electrode in each eye was referred to a needle electrode inserted subcutaneously at the level of corresponding frontal region. The different electrodes were connected to a two channels' amplifier.

After 180 min. of dark adaptation, mice were anaesthetized by an intraperitoneal injection of Avertin (1.2% tribromoethanol and 2.4% amylene hydrate in distilled water; 2 ml/100 g body weight) and loosely mounted in a stereotaxic apparatus under dim red light with the body temperature maintained at 37.5. For recordings in dark adapted conditions we adopted the following protocol: after dark adaptation ERG was recorded in response to flash of different light intensities, ranging from $1 \times 10^{-4}$ to 20 cd*m-2 sec-1. The time interval between each stimulus was 4-5 min. Amplitudes of a- and b-waves were plotted as function of increasing light intensities. After completion of responses obtained in dark-adapted conditions the recording session continued with the aim to dissect the cone pathway mediating the light response. To this aim the ERG in response to light of 20 cd*m-2 sec-1 was recorded in the presence of constant light background set at 20 cd*m-2.

In a different group of mice scotopic ERG was recorded in response to light of 1 cd*m-2 sec-1. For screening purpose 10 different responses were averaged with an interstimulus interval of 2-4 sec. Mice were then exposed to a constant light whose intensity was set at 600 cd/$m^2$ for 3 minutes (pre-adapting light, bleaching condition). Recovery of b-wave was monitored at fixed intervals after pre-adapting light (0, 5, 15, 30, 45, 60, 75 min). The amplitude of b-wave in response to a flash of 1 cd*m-2 sec-1 after the pre-adapting light was measured and expressed as relative value respect to that measured before the pre-adapting light.

Data were statistically analyzed using the Statistica (Statsoft, USA: two-way ANOVA using least significance difference test for pair-wise comparisons).

Ultrastructural analysis of the Oa1−/− retinal pigment epithelium. Oa1−/− eyes injected with AVV2/1-CMV-Oa1+ AVV2/1-EGFP (right eyes) and AVV2/1-EGFP (left eyes) were removed and fixed in 2.5% glutaraldehyde (PolyScience Inc., Eppelheim, Germany) in Cacodylate buffer 0.1M (Sigma-Aldrich, St. Louis, Mo.). The injected portion of the retina was identified with a dissecting microscope equipped with epifluorescence illumination. The EGFP positive region was dissected and processed for electron microscopy analysis, as described [30]. Briefly, the dissected tissue was fixed 2 hrs in 2.5% glutaraldehyde in Cacodylate buffer 0.1M, post-fixed 2 hrs in 1% Osmium tetroxide (Electron Microscopy Science, Hatfield, Pa.) in Cacodylate buffer 0.1M, and en bloc stained 2 hr with 1% Uranyl Acetate (Electron Microscopy Science, Hatfield, Pa.), at room temperature. Samples were then dehydrated through graded Ethanol series and Propylene Oxide (TAAB Laboratories Equipment Ltd, Aldermaston, England), and embedded in Poly-Bed (PolyScience Inc., Eppelheim, Germany) epoxy resin. Ultrathin sections were obtained from two different areas of the RPE (peripheral and central retina) in each sample. For each area two series of sections at 60 μm distance from each other were collected. Samples were analyzed with a FEI Tecnai 12-G2 TEM and FEI AnalySYS software (FEI Company, Eindhoven, The Netherlands). We analyzed the RPE of 2-months old mice. The analysis was performed on a total of ~800 μ$m^2$ for each series of sections, calculated with the "closed polygon" option of the software. We determined the density of total stage IV melanosomes (number of melanosome/$\mu m^2$), and the diameter of stage IV melanosomes, calculated along the major axis of the organelle. We measured the diameter of melanosomes completely enclosed in each micrograph.

REFERENCES

1. King, R. A., Hearing, V. J., Creel, D. J., and Oetting, W. S. (2001). Albinism. *The Metabolic and Molecular Bases of Inherited Disease*. McGroaw-Hill, New York.
2. Oetting, W. S. and King, R. A. (1999). Molecular basis of albinism: mutations and polymorphisms of pigmentation genes associated with albinism. *Hum Mutat* 13: 99-115.
3. Creel, D. J., Summers, C. G. and King, R. A. (1990). Visual anomalies associated with albinism. *Ophthalmic Paediatr Genet* 11: 193-200.
4. O'Donnell, F. E., Jr., Hambrick, G. W., Jr., Green, W. R., Iliff, W. J. and Stone, D. L. (1976). X-linked ocular albinism. An oculocutaneous macromelanosomal disorder. *Arch Ophthalmol* 94: 1883-1892.
5. Garner, A. and Jay, B. S. (1980). Macromelanosomes in X-linked ocular albinism. *Histopathology* 4: 243-254.
6. Yoshiike, T., Manabe, M., Hayakawa, M. and Ogawa, H. (1985). Macromelanosomes in X-linked ocular albinism (XLOA). *Acta Derm Venereol* 65: 66-69.
7. Bassi, M. T., et al. (1995). Cloning of the gene for ocular albinism type 1 from the distal short arm of the X chromosome. *Nat Genet* 10: 13-19.
8. Schiaffino, M. V., et al. (1996). The ocular albinism type 1 gene product is a membrane glycoprotein localized to melanosomes. *Proc Natl Acad Sci USA* 93: 9055-9060.
9. Schiaffino, M. V., et al. (1999). Ocular albinism: evidence for a defect in an intracellular signal transduction system. *Nat Genet* 23: 108-112.
10. Surace, E. M., Angeletti, B., Ballabio, A. and Marigo, V. (2000). Expression pattern of the ocular albinism type 1 (Oa1) gene in the murine retinal pigment epithelium. *Invest Ophthalmol Vis Sci* 41: 4333-4337.
11. Shen, B., Samaraweera, P., Rosenberg, B. and Orlow, S. J. (2001). Ocular albinism type 1: more than meets the eye. *Pigment Cell Res* 14: 243-248.
12. Schiaffino, M. V., et al. (2002). Effective retrovirus-mediated gene transfer in normal and mutant human melanocytes. *Hum Gene Ther* 13: 947-957.
13. Incerti, B., et al. (2000). Oa1 knock-out: new insights on the pathogenesis of ocular albinism type 1. *Hum Mol Genet* 9: 2781-2788.
14. Herrera, E., et al. (2003). Zic2 patterns binocular vision by specifying the uncrossed retinal projection. *Cell* 114: 545-557.
15. Williams, S. E., Mason, C. A. and Herrera, E. (2004). The optic chiasm as a midline choice point. *Curr Opin Neurobiol* 14: 51-60.
16. Bessant, D. A., Ali, R. R. and Bhattacharya, S. S. (2001). Molecular genetics and prospects for therapy of the inherited retinal dystrophies. *Curr Opin Genet Dev* 11: 307-316.
17. Bennett, J. (2000). Gene therapy for retinitis pigmentosa. *Curr Opin Mol Ther* 2: 420-425.
18. Auricchio, A. (2003). Pseudotyped AAV vectors for constitutive and regulated gene expression in the eye. *Vision Res* 43: 913-918.
19. Surace, E. M. and Auricchio, A. (2003). Adeno-associated viral vectors for retinal gene transfer. *Prog Retin Eye Res* 22: 705-719.
20. Rolling, F. (2004). Recombinant AAV-mediated gene transfer to the retina: gene therapy perspectives. *Gene Ther* 11 *Suppl* 1: S26-32.
21. Auricchio, A., et al. (2001). Exchange of surface proteins impacts on viral vector cellular specificity and transduction characteristics: the retina as a model. *Hum Mol Genet* 10: 3075-3081.
22. Rabinowitz, J. E., et al. (2002). Cross-packaging of a single adeno-associated virus (AAV) type 2 vector genome into multiple AAV serotypes enables transduction with broad specificity. *J Virol* 76: 791-801.
23. Yang, G. S., et al. (2002). Virus-mediated transduction of murine retina with adeno-associated virus: effects of viral capsid and genome size. *J Virol* 76: 7651-7660.
24. Kashani Z., C. B., Hawes N., Hurd R., Heckenlively J. R., Nusinowitz S. (2003). Comparison of electroretinographic responses across eleven normal in-bred mouse strains. *Invest Ophthalmol Vis Sci: ARVO E-Abstract* 44: 1896.
25. Lavallee, C. R., Chalifoux, J. R., Moosally, A. J. and Balkema, G. W. (2003). Elevated free calcium levels in the subretinal space elevate the absolute dark-adapted threshold in hypopigmented mice. *J Neurophysiol* 90: 3654-3662.
26. Behn, D., et al. (2003). Dark adaptation is faster in pigmented than albino rats. *Doc Ophthalmol* 106: 153-159.
27. Wu, J., Peachey, N. S. and Marmorstein, A. D. (2004). Light-evoked responses of the mouse retinal pigment epithelium. *J Neurophysiol* 91: 1134-1142.
28. Auricchio, A., Hildinger, M., O'Connor, E., Gao, G. P. and Wilson, J. M. (2001). Isolation of highly infectious and pure adeno-associated virus type 2 vectors with a single-step gravity-flow column. *Hum Gene Ther* 12: 71-76.
29. Liang, F. Q., Anand, V., Maguire, A. and Bennett, J. (2000). Intraocular delivery of recombinant virus. *Methods In Molecular Medicine* 47: 125-139.
30. Tavella, S., et al. (1997). Regulated expression of fibronectin, laminin and related integrin receptors during the early chondrocyte differentiation. *J Cell Sci* 110 (Pt 18): 2261-2270.

The invention claimed is:

1. A method for increasing an amount of melanosomes in a mammalian subject suffering from ocular albinism type I as compared to a non-treated subject, said method comprising:
   a) providing a recombinant adeno-associated viral (AAV) vector carrying an expression cassette which contains a nucleic acid molecule encoding an orphan G-protein coupled receptor (OA1) that crosses melanosomal membranes, wherein said nucleic acid molecule is selected from the group consisting of SEQ ID Nos. 1 and 2, and wherein said nucleic acid molecule is operably linked to a promoter selected from the group consisting of SEQ ID Nos. 3, 4, and 5; and
   b) transducing retinal pigment epithelial cells with said recombinant AAV vector by administering said vector by subretinal injection, whereby said nucleic acid molecule is expressed by the retinal pigment epithelial cells in said mammalian subject.

2. The method of claim 1, wherein said adeno-associated viral vector is of serotype 1, 2, 4 or 6.

3. The method of claim 1, wherein said promoter selected from the group consisting of SEQ ID Nos. 3, 4, and 5 is a retinal pigment epithelium-specific promoter sequence or an inducible promoter sequence.

4. The method of claim 1, resulting in improved dark adaptation of the treated subject.

5. The method of claim 1, wherein transduction of retinal pigment epithelial cells is effected by administering to the subject a pharmaceutical preparation containing the recombinant AAV vector.

6. The method of claim 5, wherein said pharmaceutical preparation is in the form of injectable solution or suspension.

* * * * *